United States Patent
Adkins, Jr.

(10) Patent No.: US 8,202,853 B2
(45) Date of Patent: Jun. 19, 2012

(54) CONVENIENCE KIT FOR EYELID TREATMENT

(75) Inventor: Nat G Adkins, Jr., Richmond, TX (US)

(73) Assignee: OCuSOFT, Inc., Rosenberg, TX (US)

( * ) Notice: Subject to any disclaimer, the term of this patent is extended or adjusted under 35 U.S.C. 154(b) by 725 days.

(21) Appl. No.: 12/346,552

(22) Filed: Dec. 30, 2008

(65) Prior Publication Data

US 2009/0137533 A1    May 28, 2009

Related U.S. Application Data

(63) Continuation-in-part of application No. 11/592,684, filed on Nov. 3, 2006, now Pat. No. 7,951,387.

(60) Provisional application No. 61/132,593, filed on Jun. 20, 2008.

(51) Int. Cl.
*A61K 31/04* (2006.01)
*A61K 31/65* (2006.01)

(52) U.S. Cl. .......................... 514/152; 514/249; 514/564

(58) Field of Classification Search .................... 424/44, 424/47, 401, 423; 514/152, 165, 249, 564
See application file for complete search history.

(56) References Cited

U.S. PATENT DOCUMENTS

| 4,344,965 | A | * | 8/1982 | Stone ............................ 514/535 |
| 5,290,572 | A | | 3/1994 | MacKeen |
| 5,713,381 | A | | 2/1998 | Sloane |
| 6,112,900 | A | | 9/2000 | Adkins, Jr. |
| 6,116,426 | A | | 9/2000 | Slonim |
| 2007/0259021 | A1 | | 11/2007 | Friedlaender et al. |

* cited by examiner

*Primary Examiner* — Michael G Hartley
*Assistant Examiner* — Jagadishwar Samala
(74) *Attorney, Agent, or Firm* — D'Ambrosio & Menon, PLLC

(57) ABSTRACT

The present invention offers an eyelid treatment kit used for convenient combination therapy for improving overall eyelid hygiene while also providing for adjunctive eyelid therapy. The eyelid treatment kit comprises low dose doxycycline hyclate tablets, a non-irritating eyelid cleansing composition, an anti-bacterial eyelid preparation and at least one pair of moist heat goggles and/or one pair of moisture chamber goggles. The eyelid treatment kit further comprises instruction sheets containing dosage and administration information on the doxycycline hyclate coupled with information on improving eyelid hygiene. The various embodiments of the eyelid treatment kit of the invention facilitate treatment of dry eyes due to infected eyelids, and proper cleansing of the eyelids to prevent recurring infections.

23 Claims, 2 Drawing Sheets

CONVENIENCE KIT FOR EYELID TREATMENT

RELATED APPLICATIONS

Priority from U.S. Provisional Patent Applications

The present application claims priority from and the benefit of U.S. Provisional Patent Application No. 61/132,593, filed Jun. 20, 2008, that is entitled "Heated Eyelid Cleanser", which is fully incorporated herein by reference.

PRIORITY FROM U.S. PATENT APPLICATIONS

The present application is a continuation-in-part (C.I.P.) application of application Ser. No. 11/592,684, filed Nov. 3, 2006 now U.S. Pat. No. 7,951,387, that is entitled "Eyelid Scrub Composition," which is fully incorporated herein by reference.

FIELD OF THE INVENTION

The present invention is related to a kit for treating ophthalmic or ocular disorders. More particularly, the present invention is a kit for treating eyelid infections and maintaining eyelid hygiene.

BACKGROUND OF THE INVENTION

The eyelids are important for ocular health because they protect the eyes from from airborne contaminants, such as pollen, dust particles or other foreign bodies. The eyelids contain several glands including the lacrimal glands and the specialized form of the sebaceous glands, the meibomian glands which produce layers of tear film that are critical for healthy eyes. It is, therefore, important to ensure that the eyelids are free of parasitical infection and clean, that is, without oil, debris, desquamated skin, bacteria, or mites that may cause infection.

SUMMARY OF THE INVENTION

A number of so-called eye infections, including dry, scratchy and irritated eyes, are caused by infected eyelids. Blepharitis is an inflammatory condition affecting the eyelids. This causes itching, burning and irritation of the eyelids. While blepharitis can be difficult to manage, following a regular eyelid hygiene routine can assist in removing the excess bacteria and toxic byproducts, including those found in cosmetics, thereby leading to a decrease in inflammation. It is also important to ensure that the meibomian glands are unclogged. The meibomian glands are located at the eyelid margins, and are responsible for the production of sebum, an oil necessary for the formation of the outer layer of the protective tear film. Clogged meibomian glands impair tear formation which in turn leads to dry eyes and other resulting eye infections, including styes, chalazions, and posterior blepharitis or meibomian gland dysfunction.

Several factors are involved in diagnosing and treating dry eyes, including tear production, quality of the tear film, lid hygiene, and even diet. The present invention offers convenient combination therapy for improving overall eyelid hygiene and also providing for adjunctive eyelid therapy. The kit of the invention comprises a tetracycline antibiotic, an eyelid cleansing composition, an anti-bacterial eyelid preparation and an eyewear apparatus. The various embodiments of the kit of the invention facilitate both treatment of infected eyelids and proper cleansing of the eyelids to prevent recurring infections and to increase tear film stability.

In one embodiment, the tetracycline antibiotic is selected from a group consisting of doxycycline, minocycline, tetracycline, oxytetracycline, chlortetracycline, demeclocycline or pharmaceutically acceptable derivatives thereof. In one aspect of the invention, the tetracycline antibiotic is preferably doxycycline. Doxycycline is used to treat a variety of microbial infections, including acne, infections of the skin and the eyelids. Doxycycline works by preventing the growth and spread of bacteria and by inhibiting collagenase and reducing inflammation. In one embodiment of the invention, doxycycline is preferably administered as its hyclate salt or as a hydrate, preferably monohydrate. Doxycycline hyclate is administered by oral ingestion, preferably in tablet or capsule form or as an oral suspension In one embodiment of the eyelid treatment kit, each doxycycline tablet comprises a low dosage, from about 15 mg to about 50 mg of doxycycline hyclate. In other aspects of the invention, the kit comprises one or more light resistant containers for the doxycycline hyclate tablets.

In one embodiment, the eyelid cleansing composition comprises a non-irritating formulation suitable for daily eyelid hygiene therapy, the non-irritating eyelid cleansing composition comprises a surfactant mixture comprising PEG-80 sorbitan laurate, sodium trideceth sulfate. PEG-150 distearate, disodium lauroamphodiacetate, cocamidopropyl hydroxysultaine, sodium laureth-13 carboxylate, sodium chloride, PEG-15 cocopolyamine, quaternium-15 and deionized water.

In one embodiment, the anti-bacterial eyelid preparation comprises polyhexamethylene biguanide, 1,2-hexanediol, 1,2-octanediol and a pH stabilizing surfactant solution present in an amount effective to control the pH level of the composition between 5.5 and 7.5.

Both the non-irritating eyelid cleansing composition and the anti-bacterial eyelid preparation can be formulated as an aqueous emulsion, a suspension, a dispersion, a foam, a cream, a lotion, a solution, a paste, a gel or a spray. In one aspect of the invention, the kit comprises one or more containers comprising either the non-irritating eyelid cleansing composition or the anti-bacterial eyelid preparation in solution form. The kit further comprises one or more applicators for applying the solution. The applicators comprise eyelid pads, disposable swabs or cotton balls. In another embodiment, the kit comprises a suitable pump dispenser for dispensing as foam either the non-irritating eyelid cleansing composition or the anti-bacterial eyelid preparation. In yet another embodiment, the kit comprises one or more pads pre-moistened with either the non-irritating eyelid cleansing composition or the anti-bacterial eyelid preparation. The pre-moistened pads can be conveniently applied to eyelids to be treated or cleansed and discarded after use. The pre-moistened pads are individually sealed and enclosed within impervious containers or packages.

In one aspect of the invention, the pads comprise an inner and outer layer. A heating element is enclosed between the inner and outer layer. The heating element generates heat by a method of heat generation selected from an exothermic chemical reaction, conductive heat transfer from an enclosed heating pouch, molecular excitation via a microwave energy source, or a combination thereof. The heat from the heated pads opens up clogged and infected meibomian glands, thereby reducing eyelid infections.

In another embodiment, the kit of the invention comprises an eyewear apparatus for treating dry eye conditions. In one aspect, eyewear apparatus comprises at least one pair of moist heat goggles, the moist heat goggles further comprising means to create heat and increase humidity around the eye to stimulate tear production and reduce the evaporation of natural tears. The moist heat goggles are specially designed to deliver moist heat directly to the orifice of the meibomian glands in order to loosen the sebum and increase the flow of healthy lipids to create a stable tear film. In another aspect of the invention, the kit comprises one or more moisture chamber goggles or glasses. Moisture chamber goggles are specially designed to retain moisture for patients suffering from dry eyes by forming a moisture chamber around the eyes.

In another embodiment, the eyelid treatment kit comprises one or more instruction sheets. The instruction sheets contain doxycycline hyclate administration and dosage information. Additionally, the instruction sheets contain information on improving eyelid hygiene and treatment using the other components of the kit.

These embodiments of the present invention, other embodiments, and their features and characteristics, will be apparent from the description, drawings and claims that follow.

DETAILED DESCRIPTION

Several problems associated with the eye, including chronic dry eyes and inflammation of the eyelids, can be traced to bacterial infection of the eyelids. It is imperative for ocular health that the eyelids are treated for these parasitical infections. At the same time, it is also important to ensure that eyelids are cleansed and adequate eyelid hygiene is maintained on an ongoing basis. The eyelid treatment kit of the invention is suitable for both adjunctive eyelid therapy and hygiene maintenance.

Figure 1A:
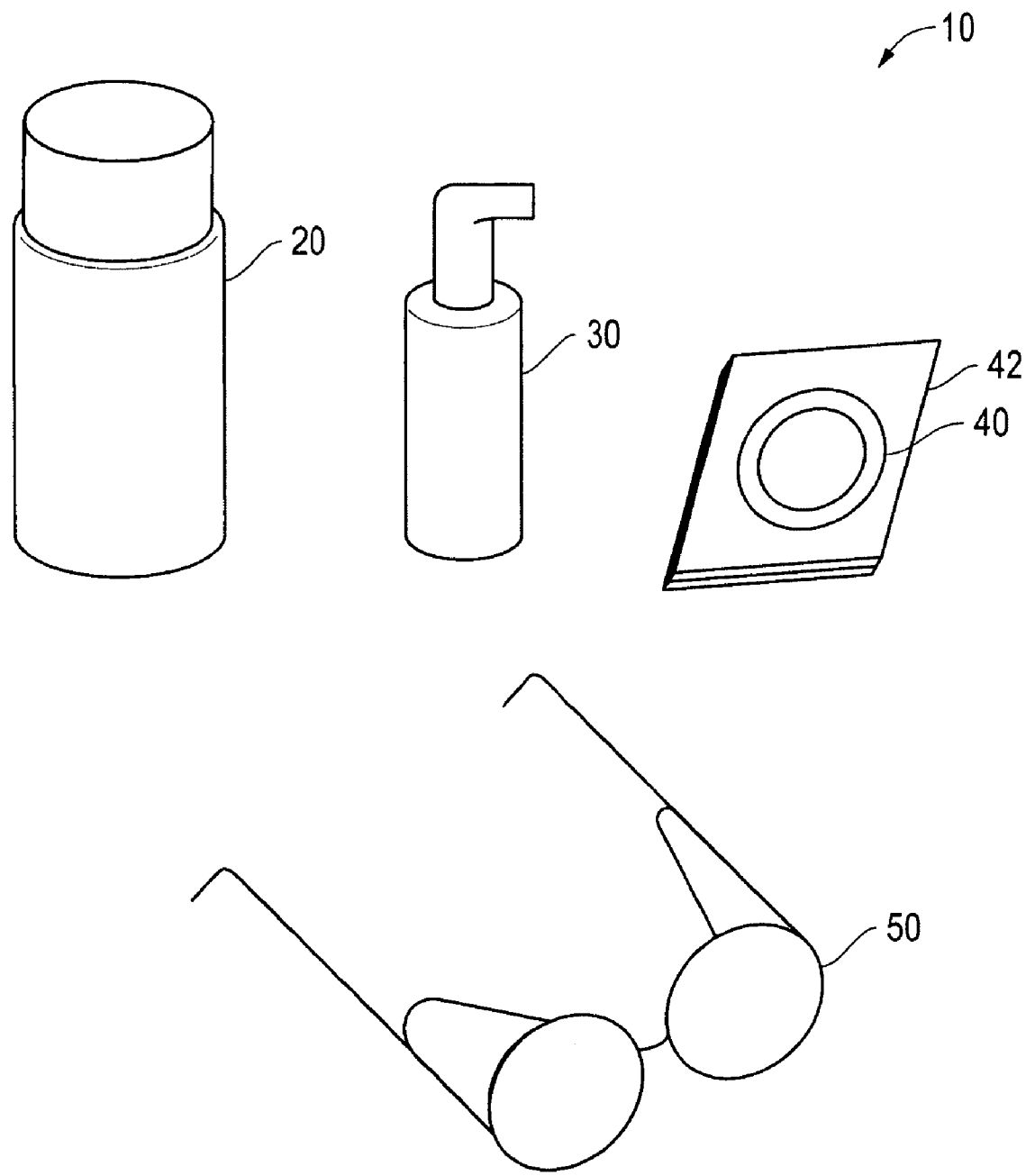
FIG. 1a depicts one embodiment of the kit of the invention.

FIG. 1a refers to one embodiment of the eyelid treatment kit 10 of the invention. The kit 10 comprises a container 20 comprising one or more doxycycline hyclate tablets. The kit 10 further comprises a pump dispenser 30 containing a non-irritating eyelid cleansing composition, one or more fabric pads 40 pre-moistened with an anti-bacterial eyelid preparation and enclosed within an impervious sealable wrapper 42 and at least one pair of moisture chamber goggles 50.

In one embodiment, the eyelid treatment kit 10 comprises low-dose doxycycline hyclate tablets stored in a light resistant container 20. In one aspect, the tablets comprise from about 15 mg to about 50 mg doxycycline hyclate. Low-dose doxycycline hyclate is a potent collagenase inhibitor. The use of low-dose doxycycline hyclate has demonstrated effective enzyme modulation treatment of inflammatory disease of the eyelids. And, at such low levels of 50 milligrams or less, it has been observed that doxycycline reduces the inflammation, yet still maintains maximum plasma drug concentrations below the anti-microbial threshold, resulting in fewer side effects such as gastritis and photosensitivity.

Doxycycline hyclate is a tetracycline antibiotic with a molecular formula of $C_{22}H_{24}N_2O_8 \cdot H_2O$ and a molecular weight of 462.46. The chemical designation for doxycycline is 4-(Dimethylamino)-1,4,4a,5,5a,6,11,12a-octahydro-3,5,10,12,12a-pentahydroxy-6-methyl-1,11-dioxo-2-naphthacenecarboxamide monohydrate. Doxycycline hyclate is soluble in water.

Doxycycline hyclate is a prescription medication. Doxycycline hyclate is used for adjunctive eyelid therapy. Doxycycline hyclate slows bacterial growth in and around the eyelids and thereby, allows the user's immune system to destroy the bacteria. Doxycycline hyclate can be administered orally as a pill, capsule, tablet or suspension. As with most prescription antibiotics, the full dosage schedule of doxycycline hyclate must be completed to avoid decreasing the drug's effectiveness and increase the chances that the bacteria may become resistant to doxycycline hyclate.

The eyelid treatment kit 10 further comprises a non-irritating eyelid cleansing composition for removing oil, debris and desquamated skin which may cause eye irritation. The non-irritating eyelid cleansing composition promotes daily eyelid hygiene which improves overall eyelid health. An exemplary non-irritating eyelid cleansing composition contains as a major ingredient about 7-10% by weight of a surfactant composition that comprises an anionic surfactant, a nonionic thickener, an emollient and an amphoteric surfactant. Preferably, the combination of surfactants comprise PEG-80 sorbitan laurate, sodium trideceth sulphate, PEG-150 distearate, cocamidopropyl hydroxy-sultaine, lauroamphocarboxy glycinate, and sodium laureth-13 carboxylate. The non-irritating eyelid cleansing composition further comprises polyoxyethylene sorbitan fatty acid ester PEG-80 sorbitan laurate, lauroamphocarboxy glycinate and sodium laureth-13 carboxylate. The non-irritating eyelid cleansing composition further comprises PEG-15 tallow polyamine in a concentration range of 0.1-0.5% by weight. This compound is a tertiary surfactant and emollient. Sodium chloride is also present in a concentration ranging from 0.6-0.9% whereby the pH of the composition will be in the range of 8.0-8.5.

In another embodiment, the non-irritating eyelid cleansing composition further comprises a preservative. The preferred preservative is quaternium-15. Quaternium-15 is present in a concentration range of 0.1-0.5%. In the alternative, benzyl alcohol may be substituted in a concentration a concentration also of 0.1-0.5%. Finally, a chelating agent such as disodium EDTA may be used in a concentration range of 0.01-0.1%.

The non-irritating eyelid cleansing composition is in a form chosen from an aqueous emulsion, a suspension, a dispersion, a foam, a cream, a lotion, a solution, a paste, a gel or a spray. In one embodiment as illustrated in FIG. 1a, the eyelid treatment kit 10 comprises a pump dispenser 30 for dispensing the non-irritating eyelid cleansing composition. The pump dispenser 30 of the kit 10 dispenses an instant foam liquid that generates pre-lathered foam immediately upon depressing its control-tip pump. This is an instant foam formula for routine eyelid hygiene or ongoing eyelid-maintenance. For convenience and economy, the size of the pump dispenser 30 can range from about a 2 fl oz bottle to a 9 fl oz bottle. A user can pump a desired amount of the non-irritating eyelid cleansing composition foam onto a clean, lint-free washcloth, or on the fingertips and gently cleanse the lids using lateral side to side strokes after which the eyelids are rinsed thoroughly. The foaming non-irritating eyelid cleansing composition provides patients who are on a lid-hygiene regimen, with added convenience.

Referring again to FIG. 1a, the eyelid treatment kit 10 further comprises an anti-bacterial eyelid preparation with a low-level preservative and moisturizer blend which offers a wide range of anti-bacterial properties for treating moderate to severe eyelid conditions. An exemplary anti-bacterial eyelid preparation comprises polyhexamethylene biguanide, 1,2-hexanediol, 1,2-octanediol and a pH stabilizing surfactant solution present in an amount effective to control the pH level of the composition between 5.5 and 7.5. The pH stabilizing surfactant solution comprises cocoamphodiacetate disodium, polyoxyethylene 80 sorbitan monolaureate, decyl polyglucoside, and a modified Ringer's solution. The modified Ringer's solution comprises sodium chloride, potassium chloride, calcium chloride and water.

The anti-bacterial eyelid preparation may be mild enough that it can be allowed to remain on the eyelid after cleansing, without rinsing. The ability of the anti-bacterial eyelid preparation to be left on the eyelid rather than be rinsed off increases the anti-bacterial eyelid preparation's anti-bacterial effect. In general, the longer the anti-bacterial eyelid preparation is allowed to contact the pathogens, the more pathogens it will kill.

The eyelid treatment kit 10 comprises one or more eyelid pads 40 pre-moistened with the anti-bacterial eyelid preparation. The pre-moistened eyelid pads 40 are dimensioned to receive a therapeutic dose, from about 1.3 grams to about 1.5 grams, of the anti-bacterial eyelid preparation. In one aspect, the pre-moistened eyelid pad 40 comprises a lint-free non-abrasive rayon and polypropylene fabric blend. In another aspect, the fabric pad 40 comprises a textured surface to absorb and retain the anti-bacterial eyelid preparation. Preferably, the fabric pads 40 further comprise a moisturizer blend that is non-drying and non-irritating. The pre-moistened fabric pads 40 are to be used in the first two weeks of the eyelid treatment or therapy or as recommended by the doctor.

One or more pre-moistened fabric pads 40 are enclosed within a sealable container 42. In one aspect, the sealable container 42 may comprise a box, or a package. The package may be made of any suitable material including plastic or a metal foil material. The pre-moistened fabric pads 40 may be individually packaged for use. The pre-moistened fabric pads 40 are applied or scrubbed on to the eyelids and other periocular regions that need to be cleansed or treated using lateral strokes. The eyelids are rinsed with water and the used fabric pads 40 are discarded.

The fabric pad 40 must be selected so that the fabric is capable of containing the anti-bacterial eyelid preparation in the interstitial spaces of fabric's weave. In one aspect, the fabric pad 40 comprises two sheets of fabric, a first sheet of fabric and a second sheet of fabric. The two pieces of fabric may be held together by stitching them together on the sides. The fabric chosen must have a textured surface which is sufficient to provide for proper scrubbing action of the eyelid cleansing composition over the user's or the patient's eyelid. However, it must remain soft enough so as to not be harsh on the user's skin. In one embodiment, the fabric pad 40 is composed of a rayon material and polypropylene fabric blend.

In another embodiment, the fabric pad 40 may be assembled in a variety of configurations to achieve the purpose of successfully applying the eyelid treatment composition to a patient's eyelid at a heated temperature. The fabric pad 40 may have either one heated moisture delivery layer or two moisture delivery layers, one heated and the other not heated. In another embodiment, the fabric pad 40 may comprise a heating element enclosed within the pad 40. The heating element may generate heat by a method of heat generation selected from exothermic chemical reaction, conductive heat transfer from an internal heating pouch, conductive heat transfer from an enclosed heating pouch, molecular excitation via a microwave energy source, or a combination thereof.

In one embodiment, heat is generated as a byproduct of an exothermic chemical reaction. In this method, the reactants may include various combinations of the chemicals butylene glycol, sodium silicoaluminate, kaolin, PEG 8, methyl gluceth 20, hydroxypropylcellulose, talc, acrylates copolymer, polyethylene, methylcellulose, ethylcellulose, BHT, tetrasodium EDTA, and ultramarines. The listed reactants may be activated causing an exothermic chemical reaction generating heat when exposed to water. In another embodiment, iron fillings may be used in place of the above mentioned reactants. The iron fillings may be activated by exposing the iron fillings to air and oxygen thereby generating heat. Another embodiment entails heating an external pouch by means of a heat transfer device such as a microwave oven and then inserting it into the fabric pad prior to administering the pad to the user or patient. The pouch of this embodiment may be configured for single or multiple uses.

The heating element provides heat to the fabric pad and the anti-bacterial eyelid preparation on the fabric pad at the start of the cleansing process, prior to applying the anti-bacterial eyelid preparation on the fabric pad 40 to the ocular area. The heat generated from the heating element is transferred to the fabric pad 40 as well as to the anti-bacterial eyelid preparation on the fabric pad 40 to enhance the efficiency of the anti-bacterial eyelid preparation because the anti-bacterial eyelid preparation is more efficient when heated and then applied to the ocular area. The heat transferred to the fabric pad 40 and the anti-bacterial eyelid preparation must be sufficient enough to bring the temperature of the anti-bacterial eyelid preparation to a temperature which aids in cleansing of the ocular area but not be too high of a temperature where it could possibly scald the patient's skin or otherwise cause discomfort. The temperature range for the heating element must be maintained in a sufficient range to enhance the cleansing process but not to cause injury to the patient. Preferably, the heating element should function to maintain the temperature of the anti-bacterial eyelid preparation and the fabric pad 40 in a range of about 80° F. to about 150° F. The heating element must be capable of sustaining heat for a sufficient enough period of time to complete the cleansing process. The exact time required for cleansing the eyelid varies from patient to patient and depends upon the severity of the patient's condition. The optimal heating and cleansing time for patients varies between a range of about 3 minutes to about 7 minutes. The heated fabric pad with the anti-bacterial eyelid preparation may then be rubbed on the eyelid, induce foaming which facilitates cleansing of the eyelid.

In another embodiment of the invention, one or more fabric pads are impregnated with the non-irritating eyelid cleansing composition while the anti-bacterial eyelid preparation may be dispensed as foam from a dispenser or solution contained in a suitable bottle or container. For the embodiments described herein, the fabric pad maybe impregnated with the non-irritating eyelid cleansing composition or the anti-bacterial eyelid preparation at the time of manufacture or moments prior to use by the user. When added at the time of manufacture, the fabric pads 40 are pre-moistened with the non-irritating eyelid cleansing composition or the anti-bacterial eyelid preparation during assembly and then sealed within a container to preserve the non-irritating eyelid cleansing composition or the anti-bacterial eyelid preparation in order to prevent it from evaporating, leaving the fabric pad 40 dry.

In another embodiment, the kit of the invention comprises an eyewear apparatus for treating dry eye conditions. Referring back to FIG. 1a, in one aspect, the kit 10 comprises at least one pair of moisture chamber goggles 50. Moisture chamber goggles 50 are specially designed glasses used in the treatment of moderate to severe dry eyes. The moisture chamber goggles 50 enclose the eye so that evaporated loss of tears is prevented. Since about 25% of tears lost are lost from evaporation, the moisture chamber goggles 50 aid in preserving tears in the eye for a longer period of time by limiting the air flow over the ocular area and thus reducing the evaporation of tears. Moisture chamber goggles 50 typically fill the space between the frame and the user's or wearer's face, thus blocking irritants and air from the eye, while trapping moisture in the eyes thereby creating a "moisture chamber" around the eyes. The moisture chamber provides a vapor barrier that acts passively to prevent tear evaporation and thereby reduce the susceptibility of the eyes to various bacterial infections.

In another aspect of the invention, the eyewear apparatus comprises at least one pair of moist heat goggles. The moist heat goggles are specially designed to deliver moist heat directly to the orifice of the meibomian glands in order to loosen the sebum and increase the flow of healthy lipids to create a stable tear film. An exemplary moist heat goggle is described in U.S. Pat. No. 7,231,922. The moist heat goggles comprise means to create heat and increase humidity around the eye to stimulate tear production and reduce the evaporation of natural tears. The moist heat goggles comprise a pair of eyecups that are capable of providing treatment to the eyes when worn. The eyecups comprise removably mounted moisture pads capable of delivering heat or cold to the ocular chamber. The desired temperature is delivered to the ocular chamber using one or a combination of means, including, microwaveable or refrigerateable gel packs, chemically activated hot and cold packs, or the moisture pad itself being formed of material that is capable of being heated or cooled.

In one aspect, ordinary wire-frame glasses can be reconfigured into moisture chamber goggles 50. Clear soft plastic side shields 52 can be attached to the glasses. In another embodiment, the shields 52 can be made of a polyurethane plastic to produce a chamber contiguous with the glasses or spectacles. An optician can then trim the side shields 52 to fit exactly to the user's face.

In one embodiment, the moisture chamber goggles 50 are adapted to define a heated chamber around the eyes to open clogged meibomian glands and thereby facilitate tear production. As the sebum in the meibomian glands is heated its properties change; its viscosity decreases allowing it to flow through narrow glandular openings and thus unclogging the meibomian glands.

Figure 1B:
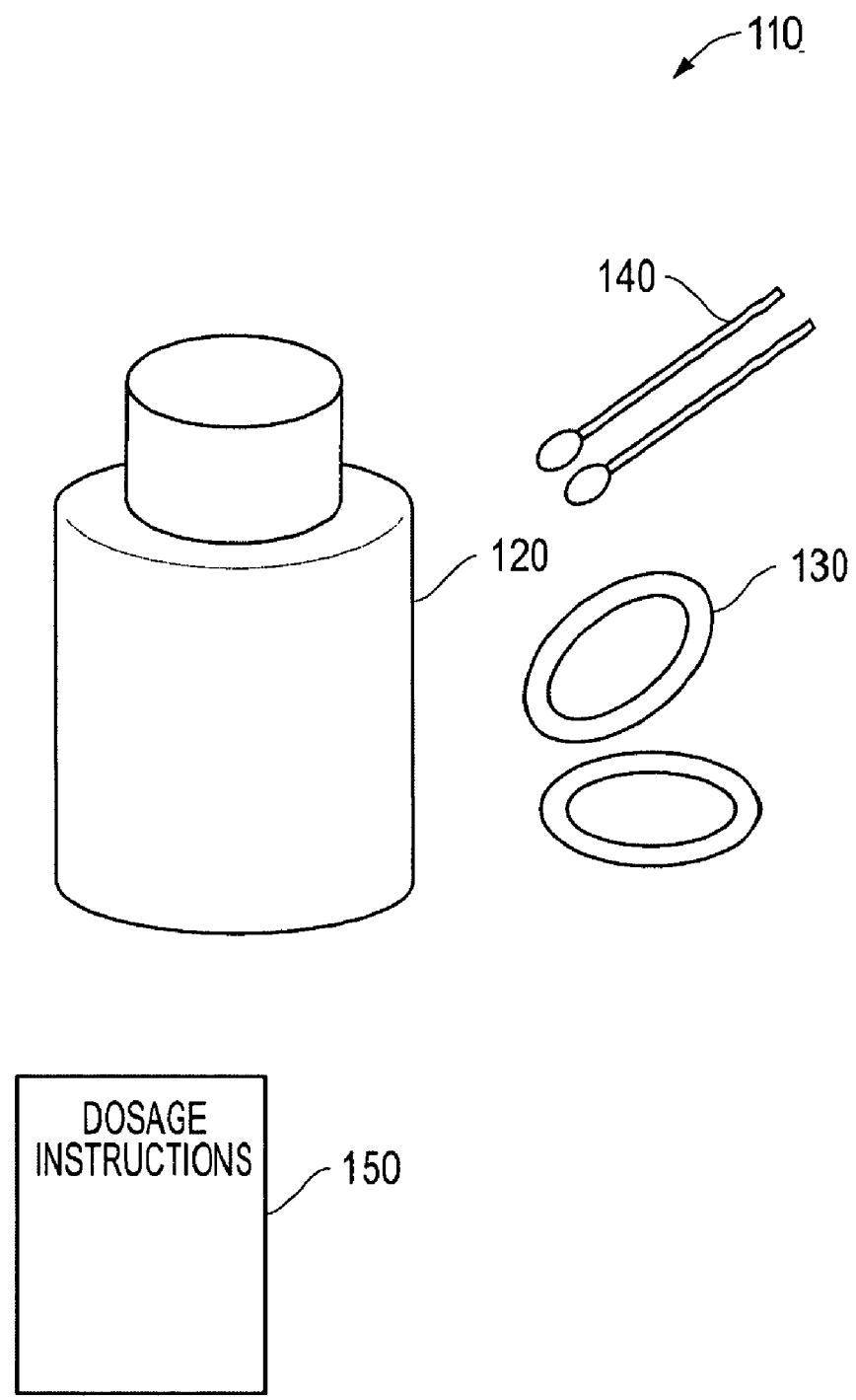
FIG. 1b depicts another embodiment of the kit of the invention.

FIG. 1*b* refers to another embodiment of the kit 110. The kit 110 comprises a container 120 comprising one of the aforementioned non-irritating eyelid cleansing composition or the anti-bacterial eyelid preparation in solution form. In one aspect, the container is selected from a glass bottle, plastic bottle or other suitable material known in the art. For convenience and economy, the bottles range in size from about 25 ml to 100 ml. The kit 110 further comprises one or more applicators for applying the non-irritating eyelid cleansing composition or the anti-bacterial eyelid preparation to the eyelids. Applicators are selected from a group comprising disposable pads 130 or swabs 140. In another aspect of the invention, paper towels, cotton balls or even the fingertips can be employed to apply the non-irritating eyelid cleansing composition or the anti-bacterial eyelid treatment preparation.

In another embodiment, the eyelid treatment kit 110 further comprises one or more instruction sheets 150 containing doxycycline hyclate tablet dosage and administration information coupled with information on improving eyelid hygiene using the various components of the kit 110. In another aspect, the dosage and administration information is provided in either instruction manuals or loose leaf paper inserts.

In another embodiment, instructions for use of the various components of the eyelid treatment kit 10, 110 are included within the kit. The instructions can be printed in a manual included within the kit 10, 110, on instruction sheets or they may be printed directly on the housing. If the instructions are printed on the housing, they may be printed on the outside of the housing or on the inside of the housing where the instructions are not visible to the user of the eyelid treatment kit 10, 110 until the user opens the kit 10, 110. As an alternative, the instructions may be printed on the containers or packaging of the individual components of the eyelid treatment kit 10, 110.

The components of the kit 10, 110 may be enclosed in suitable housing. The housing may be any type of container or means for securing the components of the eyelid treatment kit 10, 110. Preferably, the housing and various components of the eyelid treatment kit 10, 110 should be sized so that the components are secured snugly within the housing thereby preventing unnecessary movement or shifting of the various components. The housing and the components within the housing may also be sized for purposes of economy and/or convenience.

While the invention has been described with reference to preferred embodiments, the invention is not limited to the specific examples given, and other embodiments and modifications can be made by those skilled in the art without departing from the spirit and scope of the invention.

The invention claimed is:

1. An eyelid treatment kit, the kit comprising:
   a tetracycline antibiotic;
   a non-irritating eyelid cleansing composition;
   an anti-bacterial eyelid preparation; and
   an eyewear apparatus wherein the tetracycline antibiotic is doxycycline, minocycline, tetracycline, oxytetracycline, chlortetracycline, demeclocycline or pharmaceutical acceptable derivatives thereof, wherein the non-irritating eyelid cleansing composition comprises a surfactant mixture comprising PEG-80 sorbitan laurate, sodium trideceth sulfate, PEG-150 distearate, disodium lauroamphodiacetate, cocamidopropyl hydroxysultaine, sodium laureth-13 carboxylate, sodium chloride, PEG-15 cocopolyamine, quaternium-15 and deionized water; wherein the anti-bacterial eyelid preparation comprises polyhexamethylene biguanide, 1,2-hexanediol, 1,2-octanediol and a pH stabilizing surfactant solution present in an amount effective to control the pH level of the composition between 5.5 and 7.5.

2. The eyelid treatment kit of claim 1 wherein the tetracycline antibiotic is doxycycline hyclate having a molecular formula of $C_{22}H_{24}N_2O_x \cdot H_2O$.

3. The eyelid treatment kit of claim 2, wherein the doxycycline hyclate is adapted to be administered in the form of one or more tablets.

4. The eyelid treatment kit of claim 3, wherein each tablet containing from about 15 mg to about 50 mg doxycycline hyclate.

5. The eyelid treatment kit of claim 2, wherein the doxycycline hyclate is adapted to be administered in the form of a suspension.

6. The eyelid treatment kit of claim 1, wherein the non-irritating eyelid cleansing composition is in a form chosen from an aqueous emulsion, a suspension, a dispersion, a foam, a cream, a lotion, a solution, a paste, a gel or a spray.

7. The eyelid treatment kit of claim 1, further comprising a pump dispenser containing the non-irritating eyelid cleansing composition of claim 1.

8. The eyelid treatment kit of claim 1, further comprising a container comprising a solution of the non-irritating eyelid cleansing composition.

9. The eyelid treatment kit of claim 8, further comprising one or more applicators for applying the solution.

10. The eyelid treatment kit of claim 9, wherein the applicator is selected from a group consisting of a swab, a fabric pad or cotton balls.

11. The eyelid treatment kit of claim 1, wherein the anti-bacterial eyelid preparation is in a form chosen from an aqueous emulsion, a suspension, a dispersion, a foam, a cream, a lotion, a solution, a paste, a gel or a spray.

12. The eyelid treatment kit of claim 1, further comprising a fabric pad, the fabric pad pre-moistened with the anti-bacterial eyelid preparation, wherein the fabric pad is applied to the eyelids to be treated.

13. The eyelid treatment kit of claim 12, wherein the fabric pad comprises a heating element enclosed within the pad.

14. The eyelid treatment kit of claim 1, wherein the eyewear apparatus comprises at least one pair of moist heat goggles, the moist heat goggles further comprising means to create heat and increase humidity around the eye to stimulate tear production and reduce the evaporation of natural tears.

15. An eyelid treatment kit, the kit comprising:
   a container comprising one or more doxycycline hyclate tablets;
   a non-irritating eyelid cleansing composition, the non-irritating eyelid cleansing composition comprising a surfactant mixture comprising PEG-80 sorbitan laurate, sodium trideceth sulfate, PEG-150 distearate, disodium lauroamphodiacetate, cocamidopropyl hydroxysultaine, sodium laureth-13 carboxylate, sodium chloride, PEG-15 cocopolyamine, quaternium-15 and deionized water;
   an anti-bacterial eyelid preparation for treating eyelids, the anti-bacterial eyelid preparation comprising polyhexamethylene biguanide, 1,2-hexanediol, 1,2-octanediol and a pH stabilizing surfactant solution present in an amount effective to control the pH level of the composition between 5.5 and 7.5;
   at least one pair of moist heat goggles; and
   one or more instruction sheets containing doxycycline hyclate tablet dosage and administration information coupled with information on improving eyelid hygiene.

16. The eyelid treatment kit of claim 15, wherein the anti-bacterial eyelid preparation further comprises one or more moisturizers.

17. The eyelid treatment kit of claim 16, wherein the moisturizer is selected from a group consisting of methyl gluceth-20, sorbital, glycerine, glycols, propylene glycol, carboxylates, amino acids, glucoside derivatives, urea, lactates, and derivatives of pantothenic acid.

18. The eyelid treatment kit of claim 15, further comprising a pump dispenser containing the anti-bacterial eyelid preparation, wherein the anti-bacterial eyelid preparation is capable of forming a stable foam when dispersed from the pump dispenser.

19. The eyelid treatment kit of claim 15, further comprising an applicator, the applicator comprising a fabric pad with a surface area dimensioned to accommodate a therapeutic dose of the anti-bacterial eyelid preparation.

20. The eyelid treatment kit of claim 15, further comprising at least one pair of moisture chamber goggles, wherein the moist chamber goggles, when worn by a user, is adapted to define a heated chamber around the eyes to open clogged meibomian glands.

21. An eyelid treatment kit, the kit comprising:
   a light-resistant container comprising one or more low-dose doxycycline hyclate tablets, the tablets containing less than 50 mg doxycycline hyclate;
   a pump dispenser containing a non-irritating eyelid cleansing composition, the non-irritating eyelid cleansing composition comprising a surfactant mixture comprising PEG-80 sorbitan laurate, sodium trideceth sulfate, PUG-150 distearate, disodium lauroamphodiacetate, cocamidopropyl hydroxysultaine, sodium laureth-13 carboxylate, sodium chloride, PEG-15 cocopolyamine, quaternium-15 and deionized water;
   one or more fabric pads pre-moistened with an anti-bacterial eyelid preparation, the anti-bacterial eyelid preparation comprising polyhexamethylene biguanide, 1,2-hexanediol, 1,2-octanediol and a pH stabilizing surfactant solution present in an amount effective to control the pH level of the composition between 5.5 and 7.5;
   a heating element enclosed within each fabric pad;
   at least one pair of moist heat goggles and/or one pair of moisture chamber goggles; and
   one or more instruction sheets containing doxycycline hyclate tablet dosage and administration information.

22. The eyelid treatment kit of claim 21, further comprising an impervious wrapper for enclosing the pre-moistened fabric pads.

23. The eyelid treatment kit of claim 21, wherein the heating element enclosed within the fabric pads is a heat generator, the means for heat generation selected from an exothermic chemical reaction, conductive heat transfer from an internal heating pouch, conductive heat transfer from an enclosed heating pouch, molecular excitation via a microwave energy source, or a combination thereof.

* * * * *